US005952518A

United States Patent [19]

Sugiura et al.

[11] Patent Number: 5,952,518

[45] Date of Patent: Sep. 14, 1999

[54] METHOD FOR REDUCING SATURATED FATTY ACIDS FROM FATTY ACID COMPOSITIONS

[75] Inventors: Masakatsu Sugiura; Minoru Kase, both of Ibaraki, Japan

[73] Assignee: Kao Corporation, Tokyo, Japan

[21] Appl. No.: 09/069,756

[22] Filed: Apr. 30, 1998

[30] Foreign Application Priority Data

Aug. 7, 1997 [JP] Japan .................................... 9-213097

[51] Int. Cl.[6] ...................................................... C07C 51/43

[52] U.S. Cl. ............................................ 554/208; 554/211

[58] Field of Search ..................................... 554/208, 211

[56] References Cited

U.S. PATENT DOCUMENTS

| | | | |
|---|---|---|---|
| 4,792,418 | 12/1988 | Rubin et al. | 554/211 |
| 5,401,867 | 3/1995 | Sitzmann et al. . | |
| 5,556,972 | 9/1996 | Keulemans et al. | 554/211 |

FOREIGN PATENT DOCUMENTS

| | | |
|---|---|---|
| 0 378 893 | 7/1990 | European Pat. Off. . |
| 0 836 805 | 4/1998 | European Pat. Off. . |
| 57-195 | 1/1982 | Japan . |
| 60-237997 | 11/1985 | Japan . |

*Primary Examiner*—James H. Reamer
*Attorney, Agent, or Firm*—Oblon, Spivak, McClelland, Maier & Neustadt, P.C.

[57] ABSTRACT

A method for efficiently removing saturated fatty acids from a fatty acid mixture is provided by adding an emulsifying agent to a feedstock fatty acid mixture, mixing and then cooling the mixture, and removing the crystallized portion by dry fractionation, and the use of the obtained reduced saturated fatty acid level mixture to produce fatty acid esters resistant to crystallization at low temperatures.

20 Claims, No Drawings

METHOD FOR REDUCING SATURATED FATTY ACIDS FROM FATTY ACID COMPOSITIONS

BACKGROUND OF THE INVENTION

1. Field of the Invention

The present invention relates to a method for efficiently removing saturated fatty acids from fatty acid mixtures.

2. Discussion of the Background

Fatty acids are widely used as intermediates for foods, such as monoglycerides and diglycerides, and as additives and intermediates for a variety of industrial products. Such fatty acids are generally produced by hydrolyzing vegetable oils, such as rapeseed oil or soybean oil, or animal fats, such as beef tallow, under high pressure.

However, the fatty acids produced by this method alone contain saturated fatty acids derived from the fats and oils used as the feedstock. Thus it has been found that these saturated fatty acids adversely influence final products such as monoglycerides and diglycerides. For example, when a fatty acid mixture containing saturated fatty acids is used as a feedstock to produce diglycerides, the diglycerides are in a semi-solid state at room temperature and, in cold districts or in the winter, completely crystallize (solidify) to lose their flowability. These diglycerides thus have poor appearance qualities and other problems, such as difficulty in removal from containers. Oleic acid has the lowest melting point among the fatty acids which are industrially mass-produced. However, even when oleic acid is used as a feedstock for diglycerides, the final product has a melting point of about 20° C. and the above problems cannot be eliminated.

SUMMARY OF THE INVENTION

Accordingly, one object of the present invention is to provide a method for efficiently removing saturated fatty acids from a fatty acid mixture obtained from a selected feedstock for decomposition.

A further object of the present invention is to provide a method for the production of fatty acid esters that resist crystallization or solidification even at low temperatures.

These and other objects of the present invention have been satisfied by the discovery of a method based on dry fractionation (i.e., fractionation conducted without solvent) comprising adding an emulsifying agent (crystal modifier) to a feedstock fatty acid mixture, mixing and then cooling the mixture, and removing the crystallized portion. They have further found that esters produced from the above-obtained fatty acids as a feedstock have an excellent low temperature resistance to crystallization or solidification.

DETAILED DESCRIPTION OF THE PREFERRED EMBODIMENTS

The present invention relates to a method for diminishing saturated fatty acids from a fatty acid mixture, comprising adding an emulsifying agent to a feedstock fatty acid mixture, mixing and then cooling the mixture, and removing the crystallized portion by dry fractionation and to a process for producing esters, comprising reacting glycerol and the feedstock fatty acid composition having reduced levels of saturated fatty acids prepared by the above method.

The invention preferably provides a process for preparing fatty acid mixtures in which the level of saturated fatty acids have been decreased, which comprises the steps of heating and melting a starting material including fatty acids, adding an emulsifier to them, mixing the mixture, cooling it by dry fractionation to produce crystals of saturated fatty acids, removing the crystals and recovering the product fatty acids having reduced levels of saturated fatty acids. Alternatively, it is possible to add the emulsifier to the starting material and then heat the mixture or to add the fatty acid mixture and emulsifier to the reactor simultaneously and heat the mixture.

The method of the present invention is particularly effective when the amount of fatty acids contained in the feedstock fatty acid composition is 50% by weight or larger, preferably 85% by weight or larger. Partial glycerides may be present therein. Further, the present method is especially effective when used for diminishing saturated fatty acids from a fatty acid mixture derived from vegetable oils, such as rapeseed oil or soybean oil, such as a feedstock fatty acid mixture having a stearic acid content of 10% by weight or lower, preferably 5% by weight or lower. The fatty acid mixture derived from beef tallow has a stearic acid content as high as 25% by weight, and the effect of improving the filtration rate is low.

Using the present method, the cloud point of a feedstock fatty acid mixture can be lowered by at least 5° C.

Although fatty acids are used as the raw materials for various esters, the fatty acid mixture needs to be regulated from the viewpoint of the melting points of esters obtained as the final products. For the fractionation of fatty acids, solvent fractionation and wetting agent fractionation have been employed in order to improve the yield or presentation rate, but dry fractionation has not been employed because of various problems including reduced filtration rate.

In this connection, oil fractionation (dewaxing) has conventionally been widely conducted for the production of salad oil from a vegetable oil or for other purposes, and dry fractionation (solvent-free process), solvent fractionation, wetting agent fractionation, etc. are known. Among these, dry fractionation is frequently employed from the standpoints of cost, etc. A technique is also known in which various emulsifying agents are added in dry fractionation to heighten the filtration rate (JP-A 1-289897, JP-A 3-31397, and JP-A 6181686). However, these techniques are intended to be applied only to fats and oils for merely improving the filtration rate and yield to some extent, and are effective only in the removal of waxes derived from fats and oils and the compositional regulation of triglycerides.

The method of the present invention for diminishing saturated fatty acids from a fatty acid composition will be described in more detail below.

The fatty acid mixture to be used as the feedstock in the present invention are produced from vegetable oils, such as rapeseed oil or soybean oil, or animal fats, such as beef tallow, through conventional processes, such as hydrolysis by steam splitting or through hydrolysis using a lipase as the catalyst. In the present invention, it is preferred to use fatty acid mixtures in which the content of saturated fatty acids, such as palmitic acid and stearic acid, is fundamentally low, such as those derived from vegetable oils.

The present method is intended for dry fractionation using no solvents. Although the use of a solvent or an aqueous wetting agent solution improves separation efficiency, it results in an increased investment in equipment and an increased running cost necessary for the recovery of the solvent or aqueous solution, etc.

The emulsifying agent for use in the present method is preferably a polyhydric alcohol/fatty acid ester. Suitable examples include sucrose/fatty acid esters, sorbitan/fatty acid esters, propylene glycol/fatty acid esters, organic acid monoglycerides, glycerol/fatty acid esters, and polyglycerol/fatty acid esters, which are all food additives. In particular, polyglycerol/fatty acid esters are preferably used. A combination of two or more thereof may also be used. Especially preferred are those in which decaglycerol has a degree of esterification of 80% or higher.

The emulsifying agent is preferably an oleophilic one having an HLB of 7 or lower, preferably 4 or lower. Further, the emulsifying agent is preferably one which, when mixed with a fatty acid group and then cooled, precipitates spherical crystals which have an average particle diameter of preferably 50 μm or larger, more preferably 100 μm or larger. If no emulsifying agent is added, fine crystals can form a matrix to cause clogging, making filtration impossible. By growing crystals into spheres by the addition of an emulsifying agent, the voidage is increased and a sufficient filtration rate can be obtained.

The emulsifying agent is preferably added in an amount of 0.001 to 1% by weight, more preferably about 0.05 to 0.3% by weight, based on the feedstock fatty acid mixture.

In the present invention, saturated fatty acids can be diminished from a feedstock fatty acid mixture by adding an emulsifying agent to the feedstock fatty acid mixture, mixing and then cooling the mixture, and removing the crystallized portion as described above. The emulsifying agent is mixed and dissolved preferably at 30° C. or higher so as to be completely dissolved in the fatty acid mixture.

The cooling time and cooling temperature in this case are not limited, and may be selected according to the composition of the feedstock fatty acid composition. Although they vary depending on the feedstock amount, cooling capacity, etc., cooling to 0° C. for 3 to 30 hours, preferably about 15 to 25 hours, is necessary for certain feedstocks such as soybean fatty acids. The cooling may be performed using any conventional process, including either batch, continuous or semicontinuous processes.

Filtration, centrifugation, sedimentation/separation, or the like can also be used as a method for crystal separation. Similarly, these processes can be batch, continuous or semicontinuous processes.

The above-obtained product fatty acid mixture from which saturated fatty acids have been diminished is combined with glycerol and used as the feedstock to conduct ester synthesis by known methods, whereby esters which are free from crystal precipitation even at low temperatures can be produced. The present method is especially effective when the esters are diglycerides.

For obtaining diglycerides, a chemical reaction using an alkali catalyst, etc. may be conducted. However, the method described in JP-A 1-71495 is especially desirable (in which the reaction is conducted in a solvent-free system in the presence of an immobilized or intracellular lipase having 1,3-position selectivity while removing, under reduced pressure, the water yielded by the reaction), because of the mild conditions and reduced contamination of the reaction system.

The product fatty acid mixture from which saturated fatty acids have been diminished using an emulsifying agent and the esters obtained from the same contains a certain amount of the emulsifying agent dissolved therein. The emulsifying agent used can be specified through microanalysis.

EXAMPLES

Having generally described this invention, a further understanding can be obtained by reference to certain specific examples which are provided herein for purposes of illustration only and are not intended to be limiting unless otherwise specified.

Examples 1 to 8 and Comparative Examples 1 to 4

Rapeseed oil and soybean oil were hydrolyzed by a conventional method to prepare feedstock fatty acid mixtures. The fatty acid compositions of the rapeseed oil and soybean oil used are shown in Table 1.

TABLE 1

| | Fatty acid composition (wt. %) | | | | |
|---|---|---|---|---|---|
| | C16:0 | C18:0 | C18:1 | C18:2 | C18:3 |
| Rapeseed oil | 4.2 | 2.1 | 62 | 22 | 7 |
| Soybean oil | 10.4 | 4.3 | 25 | 51 | 8 |

500 g of the obtained fatty acid mixture was heated to 50° C., and 0.5 g of the emulsifying agent listed in Table 2 was added thereto. The mixture was heated at 80° C. for 15 minutes. Subsequently, the mixture was cooled at a rate of 5° C./hr under stirring at 50 rpm, and then stirred at 50 rpm for 3 hours at 5° C. for the rapeseed oil fatty acid group or at 0° C. for the soybean oil fatty acid group. Subsequently, suction filtration through filter paper having a diameter of 25 cm was conducted for a maximum of 60 minutes to examine the filtration rate, yield of liquid phase filtered, and composition of the filtered liquid. The fatty acid mixture obtained after filtration was also examined for cloud point. The results of these are shown in Table 2. The cloud point of the product rapeseed fatty acid composition was 10° C. and that of the product soybean fatty acid composition was 19° C.

The same treatment as above was conducted except that soybean oil was used in place of the fatty acid mixture, a polyglycerol/fatty acid ester (THL3, manufactured by Sakamoto Yakuhin) was used as the emulsifying agent, and the temperature for continuous cooling was changed to −5° C. The resultant mixture was filtered, and the filtrate was hydrolyzed to obtain the product soybean oil fatty acid composition, whose yield and cloud point are shown in Table 2 under Comparative Example 4.

The state of crystals (shape of crystals) after continuous cooling were examined under a microscope and photographed. With respect to each sample in which the particle size distribution of crystals could be calculated, the volume-average particle diameter thereof was determined. The results are shown in Table 3.

TABLE 2

| | Feedstock | Additive | Filtration Time | Filtration Composition C16:0 | Filtration Composition C18:0 | Yield | Cloud Point |
|---|---|---|---|---|---|---|---|
| Example 1 | rapeseed | sorbitan/fatty acid esters, B150, manufactured by Riken Vitamin | 4 min | 3.4 | 1.3 | 88 | −2° C. |
| Example 2 | rapeseed | sucrose/fatty acid ester, S3770, manufactured by Mitsubishi Chemical | 6 min | 3.4 | 1.4 | 87 | −2° C. |
| Example 3 | rapeseed | fatty acid monoglyceride, T95, manufactured by Kao | 5 min | 3.3 | 1.4 | 86 | −2° C. |
| Example 4 | rapeseed | polyglycerol/fatty acid ester, Sunsoft Q-1810S, manufactured by Taiyo Kagaku | 2 min | 3.1 | 1.1 | 90 | −4° C. |
| Example 5 | rapeseed | polyglycerol/fatty acid ester, THL3, manufactured by Sakamoto Yakuhin | 2 min | 2.9 | 1.0 | 91 | −5° C. |
| Example 6 | soybean | sorbitan/fatty acid ester, S10(F), manufactured by Kao | 12 min | 3.0 | 1.2 | 65 | −5° C. |
| Example 7 | soybean | polyglycerol/fatty acid ester, THL3, manufactured by Sakamoto Yakuhin | 10 min | 2.7 | 1.0 | 70 | −8° C. |
| Example 8 | soybean | polyglycerol/fatty acid ester, Sunsoft Q-1810S manufactured by Taiyo Kagaku | 10 min | 2.5 | 0.8 | 70 | −9° C. |
| Comparative Example 1 | rapeseed | no additive | 60 min | 3.9 | 1.7 | 55 | +6° C. |
| Comparative Example 2 | rapeseed | glycerol tristearate, manufactured by Wako Pure Chemical | 60 min | 4.0 | 1.7 | 50 | +7° C. |
| Comparative Example 3 | soybean | no additive | 60 min | 6.5 | 3.2 | 45 | +16° C. |
| Comparative Example 4 | soybean | polyglycerol/fatty acid ester, THL3, manufactured by Sakamoto Yakuhin | 60 min | 8.5 | 3.8 | 93 | +18° C. |

TABLE 3

| | Shape of crystals | Particle Diameter |
|---|---|---|
| Example 1 | spherical crystals | 65 μm |
| Example 2 | feather crystals and fine crystals | |
| Example 3 | feather crystals and fine crystals | |
| Example 4 | spherical crystals | 130 μm |
| Example 5 | spherical crystals | 120 μm |
| Example 6 | feather crystals and a minor proportion of fine crystals | |
| Example 7 | spherical crystals | 350 μm |
| Example 8 | spherical crystals | 280 μm |
| Comparative Example 1 | fine crystals | |
| Comparative Example 2 | fine crystals | |
| Comparative Example 3 | fine crystals | |
| Comparative Example 4 | fine crystals | |

Examples 9 to 12 and Comparative Examples 5 to 7

300 g of the product fatty acid composition obtained in each of Examples 4, 5, 7, and 8 and Comparative Examples 1, 2, and 3, 50 g of glycerol, and 30 g of an immobilized lipase (LIPOZYME IM, manufactured by Novo) were reacted at 40° C. under reduced pressure for 10 hours. Thereafter, the reaction mixture was distilled. The obtained diglycerides were introduced into a glass container and stored at 5° C. to evaluate their crystallization.

The evaluation was conducted in two grades; the samples which did not crystallize after one-day of storage at 5° C. are indicated by ○ and those which crystallized and solidified during one-day of storage at 5° C. (those having no flowability and unable to be taken out of the containers) are indicated by X.

As a result, the diglycerides obtained in Examples 9 to 12 from the fatty acid groups obtained in Examples 4, 5, 7, and 8 were all graded 0, whereas the diglycerides obtained in Comparative Examples 5 to 7 from the fatty acid groups obtained in Comparative Examples 1, 2, and 3 were all graded X.

Comparative Example 8

Saturated fatty acids were removed by solvent fractionation from the fatty acid composition obtained by decomposing beef tallow by a conventional method. Diglycerides were prepared from the obtained oleic acid and glycerol in the same manner as in the above Examples, and the crystallization thereof was evaluated. As a result, the product was graded X.

This application is based on Japanese Priority Applications 9-213097 and 10-76904 filed in the Japanese Patent Office on Aug. 7, 1997 and Mar. 25, 1998, respectively, the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

We claim:

1. A method for reducing saturated fatty acids from a mixture comprising fatty acids, comprising:

combining a mixture comprising at least 50% by weight of fatty acids with an emulsifying agent;

mixing and then cooling the mixture to cause crystals to form; and removing the crystallized portion by dry fractionation.

2. The method as claimed in claim 1, wherein the mixture comprising fatty acids is a mixture obtained by partial or full hydrolysis of a vegetable oil or animal fat.

3. The method as claimed in claim 2, wherein the vegetable oil is a member selected from the group consisting of rapeseed oil and soybean oil.

4. The method as claimed in claim 2, wherein the animal fat is beef tallow.

5. The method as claimed in claim 1, wherein the emulsifying agent is a polyhydric alcohol/fatty acid ester.

6. The method as claimed in claim 5, wherein the polyhydric alcohol/fatty acid ester is a member selected from the group consisting of sucrose/fatty acid esters, sorbitan/fatty acid esters, propylene glycol/fatty acid esters, organic acid monoglycerides, glycerol/fatty acid esters and polyglycerol/fatty acid esters.

7. The method as claimed in claim 6, wherein the emulsifying agent is a polyglycerol/fatty acid ester.

8. The method as claimed in claim 1, wherein the mixture comprising fatty acids contains stearic acid in an amount of 10% by weight or less.

9. The method as claimed in claim 8, wherein the amount of stearic acid is 5% by weight or less.

10. The method as claimed in claim 1, wherein the crystals are grown into spheres during the cooling step.

11. A process for producing fatty acid esters, comprising:

combining a feedstock mixture comprising at least 50% by weight of fatty acids with an emulsifying agent;

mixing and then cooling the mixture to cause crystals to form;

removing the crystallized portion by dry fractionation, to form a mixture having a reduced level of saturated fatty acids;

reacting the mixture having a reduced level of saturated fatty acids with glycerol.

12. The process as claimed in claim 11, wherein the esters thus produced are diglycerides.

13. The process as claimed in claim 11, wherein the feedstock mixture comprising fatty acids is a mixture obtained by partial or full hydrolysis of a vegetable oil or animal fat.

14. The process as claimed in claim 13, wherein the vegetable oil is a member selected from the group consisting of rapeseed oil and soybean oil.

15. The process as claimed in claim 13, wherein the animal fat is beef tallow.

16. The process as claimed in claim 11, wherein the emulsifying agent is a polyhydric alcohol/fatty acid ester.

17. The method as claimed in claim 16, wherein the polyhydric alcohol/fatty acid ester is a member selected from the group consisting of sucrose/fatty acid esters, sorbitan/fatty acid esters, propylene glycol/fatty acid esters, organic acid monoglycerides, glycerol/fatty acid esters and polyglycerol/fatty acid esters.

18. The process as claimed in claim 17, wherein the emulsifying agent is a polyglycerol/fatty acid ester.

19. The process as claimed in claim 11, wherein the feedstock mixture comprising fatty acids contains stearic acid in an amount of 10% by weight or less.

20. The process as claimed in claim 11, wherein the crystals are grown into spheres during the cooling step.

* * * * *